United States Patent [19]

Heidmueller née Degwitz et al.

[11] Patent Number: 5,314,445
[45] Date of Patent: May 24, 1994

[54] SURGICAL INSTRUMENT

[76] Inventors: Elke Heidmueller née Degwitz; Harald Heidmueller, both of Heidenrichstr. 10, D-5000 Koeln 80, Fed. Rep. of Germany

[21] Appl. No.: 930,591
[22] PCT Filed: Feb. 13, 1992
[86] PCT No.: PCT/EP92/00313
§ 371 Date: Sep. 30, 1992
§ 102(e) Date: Sep. 30, 1992
[87] PCT Pub. No.: WO92/14412
PCT Pub. Date: Sep. 3, 1992

[30] Foreign Application Priority Data

Feb. 15, 1991 [DE] Fed. Rep. of Germany ....... 4104755

[51] Int. Cl.$^5$ .............................................. A61B 17/28
[52] U.S. Cl. .................................. 606/208; 606/205; 606/174
[58] Field of Search ................ 606/170, 174, 205–209; 128/749, 751

[56] References Cited

U.S. PATENT DOCUMENTS 4,258,716  3/1981  Sutherland .
4,763,669  8/1988  Jaeger .................... 606/174
5,209,747  5/1993  Knoepfler .................. 606/208

FOREIGN PATENT DOCUMENTS 3711377   4/1987  Fed. Rep. of Germany .
980703   12/1982  U.S.S.R. ...................... 606/174

Primary Examiner—Stephen C. Pellegrino
Assistant Examiner—M. Peffley
Attorney, Agent, or Firm—Diller, Ramik & Wight

[57] ABSTRACT

A surgical instrument for performing cutting or gripping movements comprises a tube body (2) connected at its rear end with an end portion (1). The end portion is provided with a handle (4) including an actuating lever (5). At the front end of the tube body (2), are pivotable relative to each other and form a forceps. A transmission device extends from the end portion (1) to the forceps legs (9, 10) for spreading the same apart or for pressing them together. The handle (4) rotatable at the end portion (2) about an axis extending perpendicular to the axis of the tube body. Upon turning the handle (4), the transmission device (22) pivots the forceps legs (9, 10) commonly and in the same direction. Thus, it is possible to perform operations lateral of a puncture channel through which the tube body (2) extends.

7 Claims, 4 Drawing Sheets

SURGICAL INSTRUMENT

BACKGROUND OF THE INVENTION

The invention relates to a surgical instrument for performing cutting or gripping movements within a patient's body.

U.S. Pat. No. 0,003,668 describes a micro-surgery device with an elongate tube body that may be inserted into a patient's body. At the front end of the tube body, there is a stationary leg of a forceps. Cooperating with this stationary leg of the forceps is a movable leg of the forceps provided at the front end of a rod displaceable within the tube body. According to another possibility, the rod movable within the tube body is provided with two laterally resilient forceps legs that spread apart when being moved out of the tube end and that are pressed against each other when the rod is withdrawn.

There are applications, in which the instrument has to be advanced in a straight line up to the point of operation, without lateral projections protruding from the tube body. Further, it is often necessary to apply the forceps legs at sites lateral of the puncture channel through which the tube body leads. This necessity occurs in particular when vessel clamps or the like have to be set lateral of the operation site.

SUMMARY OF THE INVENTION

It is the object of the invention to provide a surgical instrument that allows to selectively perform operations in an axial orientation with the tube body and lateral thereof.

This object is solved, according to the invention, with the features mentioned in claim 1.

In the surgical instrument of the present invention, the forceps legs may be moved in two ways, namely either in opposite directions for closing and opening the forceps, or in the same direction for being pivoted laterally with respect to the tube axis. According to the respective application, the forceps legs may be designed such that they have cooperating cutting blades like the legs of a pair of scissors, or that they form a clamping forceps that is not for cutting movements, but only presses parts together bluntly. The surgical instrument may also be used to set clamps such as vessel clamps that are held by the forceps legs and are inserted into a patient's body and which are used to clamp vessels or the like inside the body. The surgical instrument may be inserted into a patient's body through a puncture channel. To this end, a pipe is provided, preferably, which is introduced first into a patient's body and keeps the puncture channel free. Thereafter, the tube body is guided to the operation site through this pipe.

For pivoting the forceps legs in the same direction, a separate actuating element may be provided at the end portion. Suitably, however, the forceps legs are pivoted in the same direction by turning the handle having the actuating element for opening and closing the forceps legs. In doing so, the handle is turned relative to the tube body, whereby the forceps legs are displaced laterally with respect to the tube body either in the one or the other pivoting direction.

The instrument allows to turn the two forceps legs in parallel such that the opening and closing operations of the forceps legs to be performed may be executed in an angular range between 0° and 90° with respect to the longitudinal axis of the tube body. In each of the pivotal positions, the forceps legs may be opened and closed by operating the actuating lever provided at the handle.

The transmission device for transmitting the force to the forceps legs may include cable controls, rods or spring wires. When using cable controls, a particularly narrow guiding of the cable controls may be provided, the tube body then having a small diameter. The cable controls may be guided by guide rollers and/or eyes. The cable controls that are guided around pivoting bodies, cause a transformation of a rotational movement into an axial movement and, at the front end of the instrument, they transform the axial movement into a rotational movement again. In order to achieve a transmission, the disc bodies arranged in the end portion are larger than those arranged in the head portion.

The following is a detailed description of an embodiment of the invention taken in conjunction with the accompanying drawings.

DESCRIPTION OF THE PREFERRED EMBODIMENTS

Figure 1:
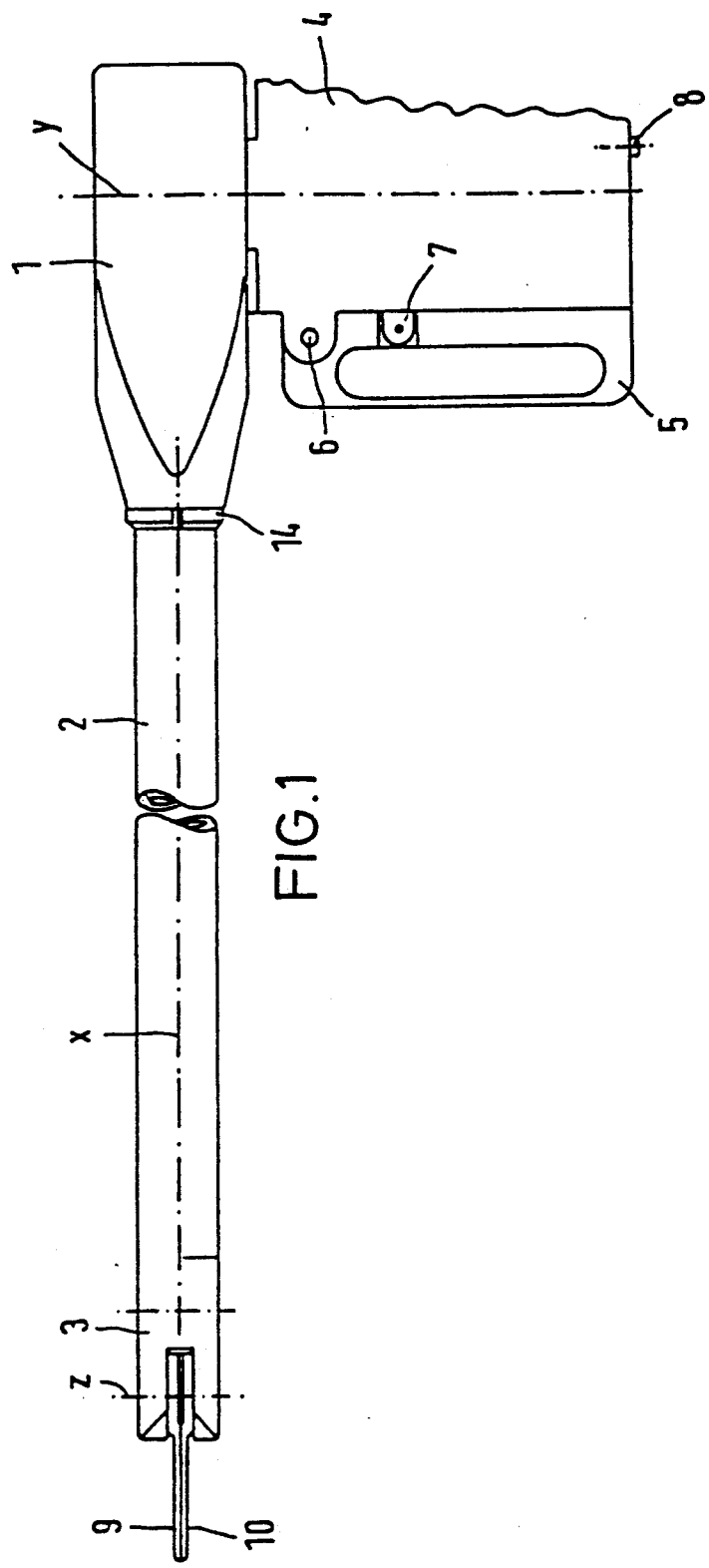
FIG. 1 is a side elevational view of the instrument.
Figure 2:
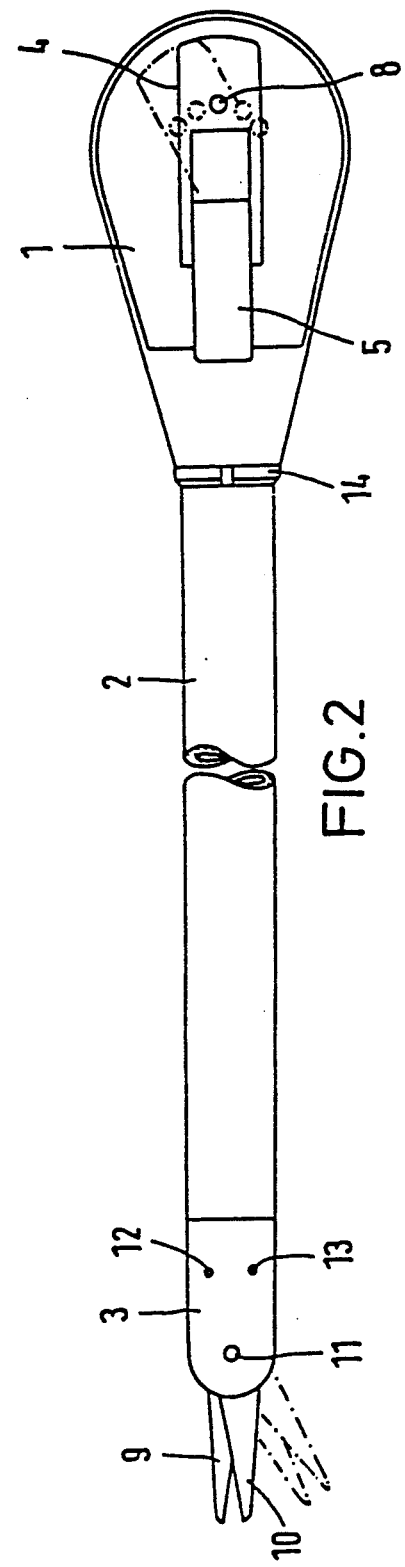
FIG. 2 is a bottom view of the instrument.

FIGS. 1 and 2 are a side elevational and a bottom view, respectively, showing the instrument comprising an end portion 1, a tube body 2 joining the same, and a head portion 3 of the same diameter as the tube body. At the bottom of the end portion 1, a handle 4 is provided that is supported in the handle portion for rotation about an axis of rotation Y extending perpendicular to the longitudinal axis X of the tube. Further details discernible are a pivotable actuating lever 5 supported in a pivot pin 6 and acting on a lug 7, and a push button 8 for operating a locking arrangement for the displacement of the handle 4. In the head portion, a pair of forceps legs 9, 10 are supported on a pivot pin 11, the legs being pivotable about an axis Z that is perpendicular to the longitudinal axis of the tube. Further pins 12, 13 in the head portion will be explained later. A union ring 14 between the tube body 2 and the end portion 1 represents the connection, secured against rotation, between these two members and may possibly allow a certain amount of a relative twist about the axis X when loosened, without influencing the function thereby. The axis Y may also form an angle other than 90° with the axis X. As illustrated in broken lines in FIG. 2, a turning of the handle 4 about the axis Y causes the forceps legs 9, 10 to commonly pivot about the axis Z. In a manner to be explained, a pivoting of the actuating lever 5 against the action of a spring causes the forceps legs 9, 10 to open and close.

Figure 4:
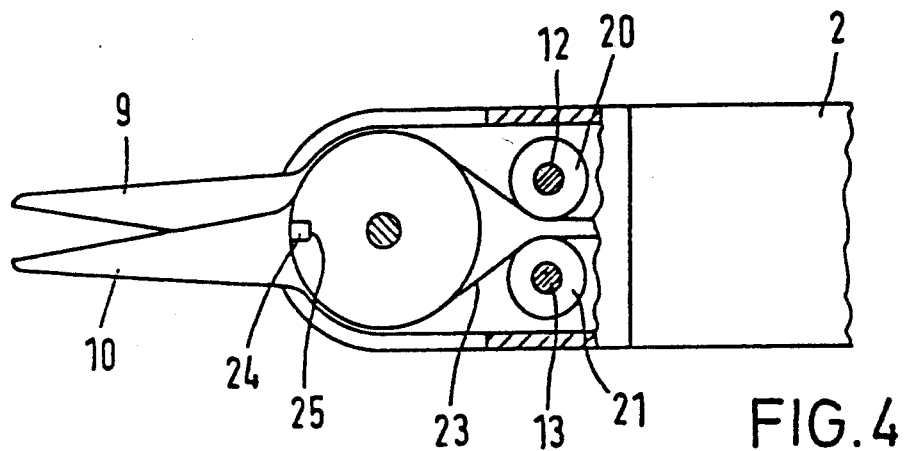
FIG. 4 is the head portion of the tube body cut in parallel to the plane of movement in the Figures.
Figure 3:
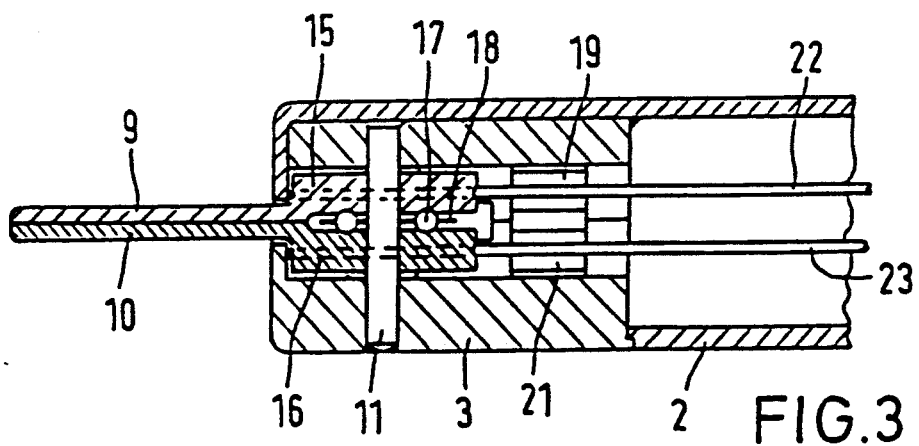
FIG. 3 is the head portion of the tube body cut perpendicular to the plane of movement in the Figures.

In FIGS. 3 and 4, the round tube body 2, as well as head portion 3 which is penetrated by a pin 11 are shown, the head portion also being round in cross section and being rounded at the front in one plane. Disc bodies 15, 16 are rotatably supported on the pin 11, to which the forceps legs 9 and 10 are fastened, respectively. Between the disc bodies 15, 16, a ball bearing 17 with a disc-shaped cage 18 is shown. On the pivot pins 12, 13, two guide rollers are rotatably supported, respectively, the rolls 19, 21 supported on pin 13 being illustrated in FIG. 5, and the lower roller 20 supported on pin 12 being illustrated in FIG. 4 in addition to the roller 21. A continuous cord 22 extends around the upper guiding rollers and the upper disc body 15. A continuous cord 23 extends around the lower guiding rollers and the disc body 16. Each of these cords is fastened in a circumferential groove 25 of the corresponding disc body by means of a nipple 24, thereby being connected with the disc body in a non-skidding manner.

Figure 5:
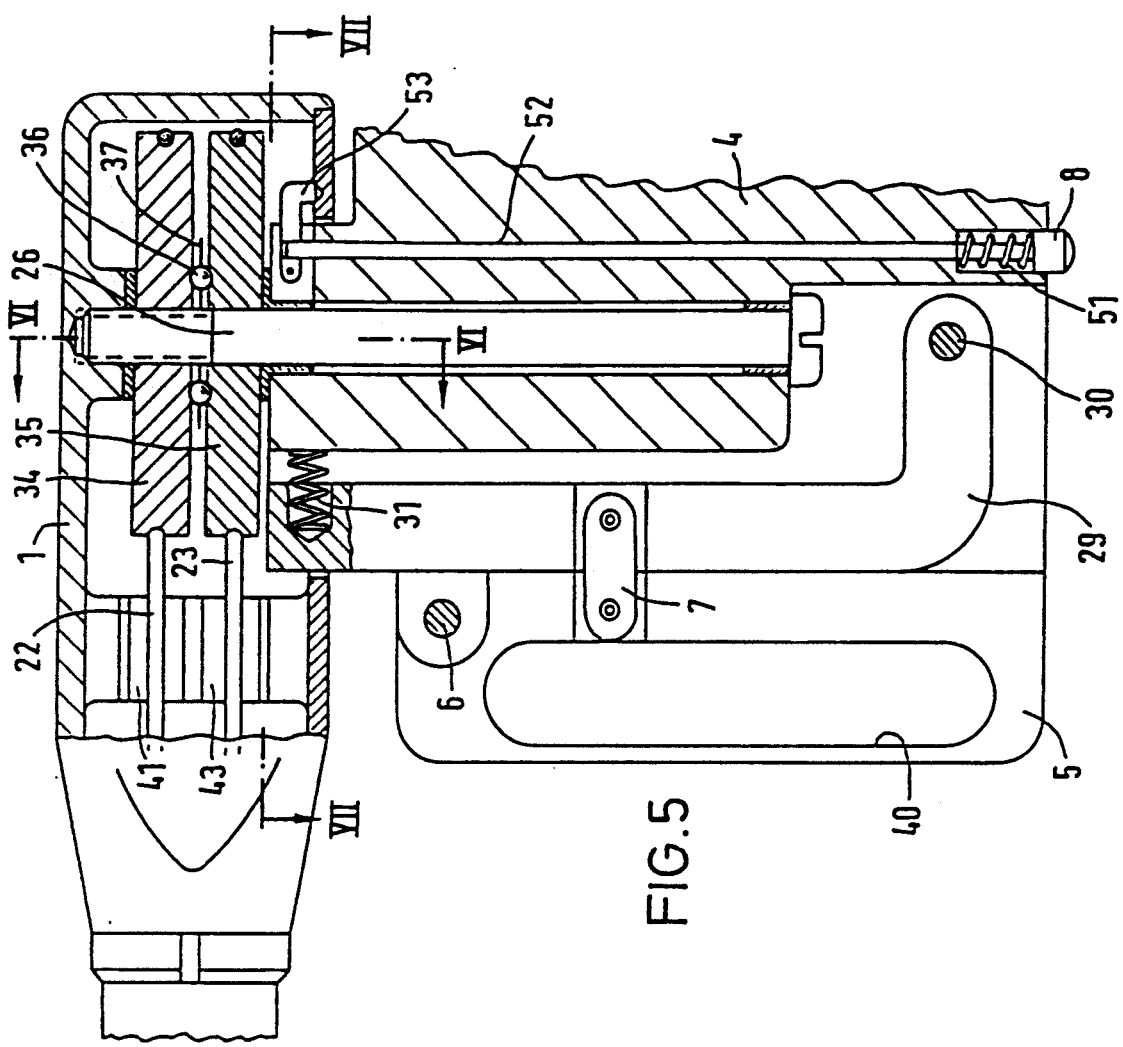
FIG. 5 is the handle member in a section through the axis of the rotatable member.
Figure 6:
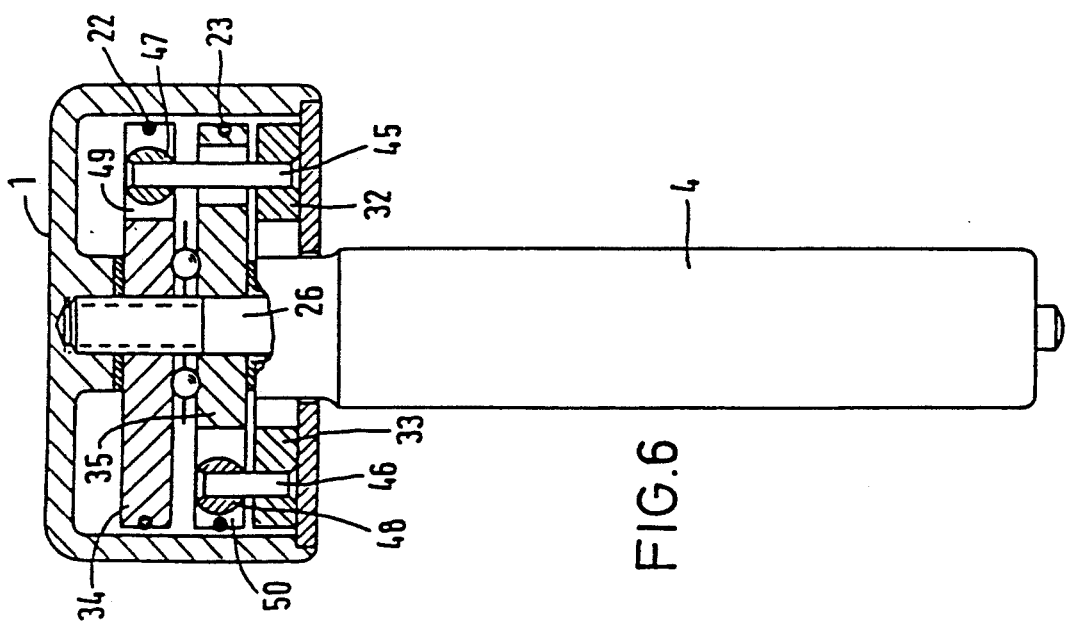
FIG. 6 is the handle member in a section through the axis of the rotatable member along line VI—VI in FIG. 5.
Figure 7:
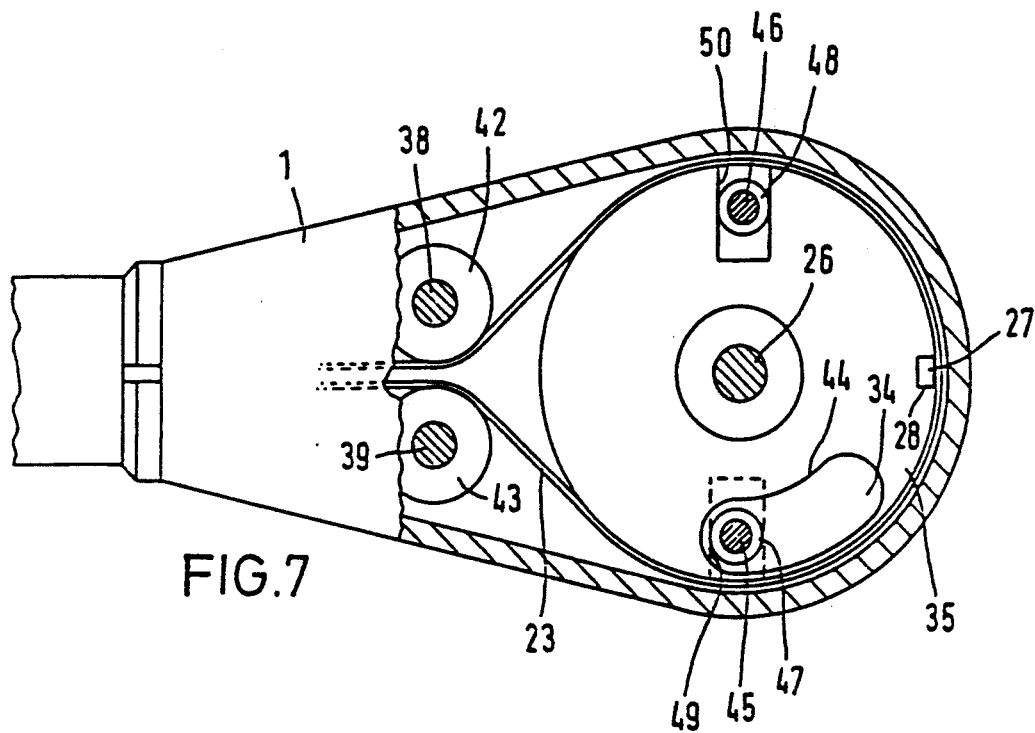
FIG. 7 is a section through the handle member along the line VII—VII in FIG. 5.
Figures 8, 9:
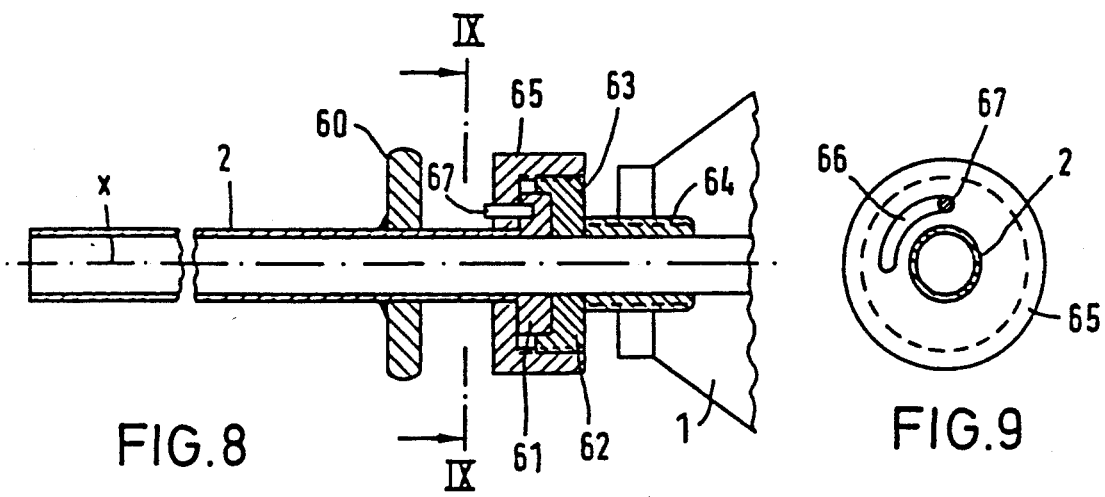
FIG. 8 shows the connection between the tube body and the end portion in a modified embodiment.
FIG. 9 is a section along line IX—IX in FIG. 8.

FIGS. 5 to 7 illustrate the end portion 1 with the handle 4 mounted thereto and being rotatably supported on a pivot pin 26 screwed into the end portion 1. A lug 7 connects the actuating lever 5 supported in the pivot pin 6 with a pressure lever 29 that is supported in a pivot pin 30 in the handle 4 and is resiliently supported at the handle 4 by at least one pressure spring 31. The pressure lever 29 branches in a yoke like manner at the free end of the lever and passes into two symmetrical yoke ends 32, 33 that are connected with the pressure lever 29 in a constant angle relative to the axis of rotation Y. Also rotatably supported on the pivot pin 26, there are two disc bodies 34, 35 between which a ball bearing 36 with a disc-shaped cage 37 is arranged. Further, two pairs of respectively superimposed guiding rollers are supported on two pivot pins 38, 39 within the handle, the guiding rollers 42, 43 being illustrated in FIG. 7, while the guiding rollers 41 and 43 supported on the pin 39 are shown in FIG. 8. The upper continuous cord 22 extends around the upper guiding rollers and the disc body 34 and the lower continuous cord 23 extends around the lower guiding rollers and the disc body 35. On the rear sides of the disc bodies nipples 27 are arranged, respectively, which engage circumferential grooves 28 of the disc bodies and connect the cable controls with the disc bodies in a non-skidding manner.

Pins 45, 46 of different lengths are respectively inserted into the yoke ends 32, 33, on the ends of which pins ball heads 47, 48 are rotatably or fixedly arranged in order to reduce friction. These ball heads engage radial lateral slits 49, 50 of the disc bodies 34, 35. The lower disc body 35 is provided with a circumferential slot 44 through which the pin 45 passes and engages the slit 49 of the upper disc body 34. The push button 8 in the handle presses against a pressure spring 51 and, via a push rod 52, acts on a one-armed locking lever 53 that may inhibit or enable the rotatability of the handle 4 relative to the handle member 1 by engaging corresponding notches in the handle member.

When the push button 8 is depressed and the entire handle 5 is turned about the axis of rotation Y on the pivot pin 26, the disc bodies 34, 35 are simultaneously turned in the same direction by virtue of the pins 45, 46 inserted into the yoke ends 32, 33 of the pressure lever 29. Via the various guiding rollers, this causes the forceps legs 9, 10 to turn in the same direction, without them moving relative to each other. In the desired position, the handle 4 may be locked relative to the end portion 1 so that the forceps legs are adjusted in an operating position. Upon exerting a pressure on the actuating lever 5, which is transferred onto the pressure lever 29, the yoke ends 32, 33 respectively move in the same direction and parallel to the lever plane or the central plane of the handle 4, whereby the disc bodies 34, 35 are turned by the same angle in opposite directions relative to the axis of rotation Y, thereby being turned relative to each other. The pins 45, 46, respectively performing a linear movement with their ball pins 47, 48, move relatively in a radially outward direction within the radial slots 48, 50. At the same time, the pin 46 moves in the circumferential direction relative to the circumferential slot 44. The relative movement between the disc bodies 34, 35 is transferred correspondingly onto a relative movement of the disc bodies 16, 17, thereby causing a cutting or clamping movement of the forceps legs 9, 10, the same opening against the action of the spring 21 and closing due to the action of the spring. Since the actuator handle 5 has a closed eye 50, a resetting of the spring may be dispensed with entirely and it is possible to manually set and maintain any opening position of the forceps legs by the mechanical restricted guidance.

The cords of the cable controls are guided in solid eyes within the tube body. Within the tube body, there may also be arranged means for tensioning the cords, e.g., rope winders with two oppositely directed threads, between cord portions to be connected.

An embodiment for the tensioning of the tube body 2 for adjustment to changes in the lengths of the cable controls and for turning the tube body 8, and thereby the forceps legs, about the axis X of the tube body 2, is shown in FIGS. 8 and 9. Near its rear end, the tube body 2 is provided with a handle 60 for manually turning the same about the axis X. At the rear end of the tube body 2, there is a flange 61 that presses on the head 62 of an adjustment screw 63. The adjustment screw 63 has a threaded shaft 64 screwed into an inner thread of the end portion 1, the depth of the screwing being adjustable by turning the adjustment screw 63. A swivel nut 65 is screwed onto an outer thread of the flange 62, the nut encompassing the flange 61 of the tube body 2 and having its front wall press this flange against the head 62 of the adjustment screw 63.

By turning the swivel nut 65, the screwing depth of the threaded shaft 64, and thereby the effective length of the tube body 2, may be changed in order to tension the cable controls 22 and 23 extending within the tube body.

In the front wall of the swivel nut 65, a sector-shaped oblong hole 66 is provided into which a pin 67 projects from the flange 61. When holding the swivel nut 65 with the hand, the tube body 2 may be rotated by 90° about the axis X by grasping the handle 60. Thus, it is possible to pivot the forceps legs synchronous with each other about two axes extending rectangularly with respect to each other.

The entire surgical instrument consists of a sterilisable material, preferably of metal. Also the cable controls consist of metal wires. If the sterilisation is effected with vapor at 134° C., the cable controls consisting of multiple thread wires become longer due to the thermal stress so that an adjustment is required for tensioning the cable controls. This adjustment is effected by turning the unit formed by the adjustment screw 63 and the swivel nut 65 in the thread of the end portion 1.

We claim:

1. A surgical instrument for performing cutting or gripping movements, comprising
   a tube body (2) having an axis and an end portion (1) at its rear end, said end portion (1) having a handle (4) including an actuating lever (5),
   a forceps disposed at the front end of said tube body (2) and comprising a pair of forceps legs (9, 10) that are pivotable relative to each other, and
   a transmission device extending from said end portion (1) through said tube body (2) to said forceps for pivoting said forceps legs (9, 10), said device further being coupled to said actuating lever for spreading said forceps legs (9, 10) apart or for pressing them together in dependence of the movements of said actuating lever (5),
   characterised in
   that said handle is provided with supporting means to allow for the rotation of said handle about an axis which is generally normal to said tube body axis, such that rotation of said handle about said normal axis pivots said forceps legs commonly and in the same direction.

2. The surgical instrument of claim 1, wherein said forceps legs (9, 10) are secured to superimposed pivot bodies (15, 16), said transmission device (22, 23) engaging said pivot bodies (15, 16) tangentially, and said pivot bodies (15, 16) being rotatable in opposite directions by moving said actuating lever (5).

3. The surgical instrument of claim 1, wherein said actuating lever (5) is coupled to superimposed pivot bodies (34, 35) and said last-mentioned pivot bodies (34, 35) are engaged tangentially by said transmission device (22, 23).

4. The surgical instrument of claim 3, wherein said actuating lever (5) is coupled to a pair of parallel pins (45, 46) that engage opposite radial slots (49, 50) of said superimposed pivot bodies (34, 35) and are commonly movable in the longitudinal direction of said tube body (2) for turning said superimposed pivot bodies (34, 35) in opposite directions, and wherein the pivot body (35) faces said handle (4) and has a circumferential slot (44) for the passage of said pin (45) for the pivot body (34) averted from said handle (4).

5. The surgical instrument of claim 1, wherein said transmission device (22, 23) includes cable control (22; 23) for moving each of said forceps legs (9, 10).

6. The surgical instrument of claim 1, wherein releasable locking device means (8, 52, 52) is provided between said rotatable handle (4) and said end portion (1) for selectively locking said handle (4).

7. The surgical instrument of claim 1, wherein rotary adjustment means (14) is provided between said tube body (2) and said end portion (1) for effecting limited rotational adjustment therebetween.

* * * * *